United States Patent
Neer

(10) Patent No.: US 8,431,074 B2
(45) Date of Patent: Apr. 30, 2013

(54) ULTRAVIOLET TUBING AND TIP STERILIZER

(75) Inventor: Charles S. Neer, Cincinnati, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 12/996,466

(22) PCT Filed: Jul. 28, 2009

(86) PCT No.: PCT/US2009/051933
§ 371 (c)(1),
(2), (4) Date: Dec. 6, 2010

(87) PCT Pub. No.: WO2010/014590
PCT Pub. Date: Feb. 4, 2010

(65) Prior Publication Data
US 2011/0125013 A1    May 26, 2011

Related U.S. Application Data

(60) Provisional application No. 61/084,554, filed on Jul. 29, 2008.

(51) Int. Cl.
*A61L 2/00*    (2006.01)
*A61M 37/00*   (2006.01)

(52) U.S. Cl.
USPC ............................................ 422/24; 604/131

(58) Field of Classification Search ............ 604/29, 604/131; 250/455.11; 422/24
See application file for complete search history.

(56) References Cited

U.S. PATENT DOCUMENTS

| | | | |
|---|---|---|---|
| 4,433,244 A | | 2/1984 | Hogan |
| 4,500,788 A | * | 2/1985 | Kulin et al. ............... 250/455.11 |
| 4,503,333 A | * | 3/1985 | Kulin et al. ............... 250/455.11 |
| 4,620,845 A | * | 11/1986 | Popovich et al. ............... 604/28 |
| 4,882,496 A | | 11/1989 | Bellotti et al. |
| 5,885,216 A | | 3/1999 | Evans, III et al. |
| 6,623,455 B2 | * | 9/2003 | Small et al. ................... 604/131 |
| 6,901,283 B2 | * | 5/2005 | Evans et al. ................... 600/431 |
| 7,834,328 B2 | * | 11/2010 | Redmond et al. ......... 250/455.11 |
| 8,157,761 B2 | * | 4/2012 | Sobue et al. .................... 604/29 |
| 8,197,087 B2 | * | 6/2012 | Sobue et al. .............. 362/249.02 |
| 2001/0009994 A1 | | 7/2001 | Small et al. |
| 2003/0017073 A1 | | 1/2003 | Eckhardt et al. |
| 2007/0100282 A1 | * | 5/2007 | Small et al. ................... 604/151 |
| 2007/0176117 A1 | | 8/2007 | Redmond et al. |
| 2008/0027399 A1 | | 1/2008 | Harding et al. |
| 2008/0058720 A1 | | 3/2008 | Spohn et al. |
| 2009/0012451 A1 | | 1/2009 | Sobue et al. |

FOREIGN PATENT DOCUMENTS

EP    1 532 989    5/2005

* cited by examiner

*Primary Examiner* — Victoria P Shumate
(74) *Attorney, Agent, or Firm* — Marsh, Fischmann, & Brey Fogle LLC

(57) ABSTRACT

An injection system (108) includes a sterilization port (130) operable to sterilize a tube set connector (116) inserted therein. The sterilization port (130) may include a single sterilization port opening (132) through which the tube set connector (116), in an unconnected state, may be inserted. The sterilization port (130) may include an ultraviolet light source (158) capable of irradiating the tube set connector (116) with ultraviolet radiation when the tube set connector (116) is disposed within the sterilization port (130). The sterilization port (130) may include a movable member or door (136) capable of closing around the inserted tube set connector (116) and/or a tubing (118) connected to the tube set connector (116) to reduce the amount of ultraviolet light that may escape from the sterilization port (130). A sensor (194) may be included to determine if the tube set connector (116) has been inserted into the sterilization port (130).

25 Claims, 8 Drawing Sheets ately interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

ULTRAVIOLET TUBING AND TIP STERILIZER

CROSS-REFERENCE TO RELATED APPLICATIONS

This patent application claims priority under 35 U.S.C. §119(e) to pending U.S. Patent Provisional Patent Application Ser. No. 61/084,554 entitled "ULTRAVIOLET TUBING AND TIP STERILIZER" filed on Jul. 29, 2008.

FIELD OF THE INVENTION

The present invention generally relates to injection systems and more particularly to injection systems with ultraviolet tubing/tip sterilizers.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

The syringes used by the power injector may be pre-filled and/or bulk fluid containers may be used to fill the syringes of the power injector. Where bulk fluid containers are utilized, the syringes may be filled by retracting the plunger of the syringe while the bulk fluid container is fluidly interconnected with the syringe. This may be desirable since bulk fluids (e.g., multiple doses of fluids supplied in a single bulk container) may be less expensive to use than individually filled, one time use syringes.

One example of a medical procedure involving the injection of fluids is an imaging procedure such as a radiological procedure used to image the internal structure of a patient (e.g., computed tomography or CT imaging; magnetic resonance imaging or MRI; SPECT imaging; PET imaging; X-ray imaging; angiographic imaging; optical imaging; ultrasound imaging). To aid in the imaging, contrast may be injected into the patient. Typically, contrast is supplied in individual syringes of a predetermined volume.

SUMMARY

A first aspect of the present invention is provided by an injection system that includes a power injector, a tube set, and a sterilization port including an ultraviolet light source. The tube set is fluidly interconnected to the power injector and includes a tube set connector. The ultraviolet light source is disposed within an interior of the sterilization port. The sterilization port is operable to receive the tube set connector in an unconnected state. The sterilization port may be used to kill or inactivate organisms on the tube set connector when the tube set connector is inserted therein through exposure to ultraviolet light emitted from the ultraviolet light source. For example, where a syringe of an injection system is filled from a reservoir (e.g., a bulk fluid source) prior to being fluidly interconnected with a patient, a tube set connector fluidly interconnected with the reservoir may be used to sequentially fluidly interconnect with multiple syringes. In such a system, the tube set connector may be disposed within the sterilization port and the ultraviolet light source illuminated between successive connections to the syringes to be filled. In another example, where a syringe of an injection system is used to intermittently deliver fluids to a patient and the injection system is disconnected from the patient between the intermittent fluid deliveries, a connector used to interconnect the injection system to the patient may be disposed within the sterilization port and the ultraviolet light source illuminated prior to each reconnection to the patient. In another example, where an injection system is used to inject fluids into a plurality of patients in succession (e.g., where a unique patient-specific tube set is interconnected to each patient and a multi-use tube set of the injection system is fluidly interconnected to each patient-specific tube set in succession), a connector of the multi-use tube set that fluidly interconnects to the patient-specific tube sets may be disposed within the sterilization port and the ultraviolet light source illuminated prior to each connection to a patient-specific tube set.

A number of feature refinements and additional features are applicable to the first aspect of the present invention. These feature refinements and additional features may be used individually or in any combination. As such, each of the following features that will be discussed may be, but are not required to be, used with any other feature or combination of features of the first aspect. The following discussion is applicable to the first aspect, up to the start of the discussion of a second aspect of the present invention.

The injection system may include illumination control logic operable to control the ultraviolet light source. The injection system may include timing logic operable to illuminate the ultraviolet light source for a predeterminable length of time. The predeterminable length of time may be calculated to kill or inactivate a predetermined percentage of microorganisms that may be disposed on the tube set connector.

The injection system may include a movable member or door operable to close around a tube of the tube set when the tube set connector is disposed within the sterilization port. In this regard, a user may insert the tube set connector into the sterilization port and then the door may close (manually or automatically) around a portion of the tube set to obstruct ultraviolet light source that would otherwise escape from the sterilization port. The illumination control logic may be operable to prevent the ultraviolet light source from illuminating the interior when the door is in an open position. The illumination control logic may be operable to energize the ultraviolet light source to illuminate the interior when the door is in a closed position.

A tube set holder may be included in the injection system. The tube set holder may be disposed at an opening of the sterilization port, and may be operable to secure the tube set such that a position of the tube set connector within the sterilization port is maintainable. The sterilization port may include a reflective lining. The ultraviolet light source may be operable to emit ultraviolet energy within the 200 nm to 280 nm wavelengths.

The injection system may include a tube set detection member (e.g., a sensor) operable to detect a portion of the tube set (e.g., the tube set connector) disposed within the sterilization port. The illumination control logic may be operable to energize the ultraviolet light source to illuminate the interior when the tube set detection member detects the portion of the tube set disposed within the sterilization port. The illumination control logic may be operable to automatically illuminate the ultraviolet light source upon an insertion into the sterilization port.

The injection system may further include a locking mechanism operable to lock the tube set into place when a portion of the tube set (e.g., the tub set connector) is disposed within the sterilization port and the ultraviolet light source is illuminated. The injection system may further include a timing module operable to illuminate the ultraviolet light source after the tube set connector has been disposed within the sterilization port for a predeterminable period of time.

The sterilization port may be in the form of a blind opening. In this regard, the blind opening may be the only opening to the interior of the sterilization port through which the tube set connector may be inserted. The blind opening may correspond to a cross section (e.g., perpendicular to the direction of fluid flow through the connector) of the tube set connector. The blind opening may be configured such that the tube set connector is inoperable to pass into the sterilization port when the tube set connector is in a connected state. The sterilization port may be disposed within a housing of the injection system. The blind opening may extend through a single face of the housing.

The tube set connector may include a lumen passing therethrough, and the lumen may be disposed along an axis of the tube set connector. The tube set connector and sterilization port may be configured such that the tube set connector is only operable to enter the interior by advancing the tube set connector along the axis.

The injection system may include a fluid source. In an arrangement, the tube set may be fluidly interconnected with the fluid source, and the tube set connector may be fluidly interconnectable with a syringe mounted on the power injector. In an arrangement, the tube set may be fluidly interconnected with the fluid source as well as a power injector syringe, and the tube set connector may be fluidly interconnectable with a patient-specific tube set. Similarly and regardless of whether a fluid source is utilized by the injection system, the tube set may be in the form of a multi-use or multi-patient tube set, may be fluidly interconnected with a syringe of the power injector, and the tube set connector may be sequentially fluidly interconnectable with a number of patient-specific or single-use tube sets (the tube set connector being sterilized prior to establishing a connection with each such patient-specific tube set).

The injection system may include a button or other appropriate input device (e.g., disposed proximate to the sterilization port) that when activated by a user, would cause the illumination control logic to energize the ultraviolet light source. In this regard, a user may initiate the sterilization of a tube set connector disposed within the sterilization port.

A second aspect of the present invention is provided by a sterilization device that includes a housing, a sterilization chamber disposed within the housing, an ultraviolet light source, a blind hole extending into the housing and into the sterilization chamber, a movable member, and illumination control logic. The ultraviolet light source is operable to illuminate the sterilization chamber with ultraviolet light. The blind hole is the only hole extending into the housing and into the sterilization chamber. In a first position, the movable member is free from interference with the blind hole. In a second position, the movable member partially covers the blind hole. The illumination control logic is operable to prevent the ultraviolet light source from being illuminated when the movable member is in the first position, and the illumination control logic is operable to energize the ultraviolet light source to illuminate the sterilization chamber when the movable member is in the second position.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect. The following discussion is applicable to the second aspect, up to the start of the discussion of third, fourth, and fifth aspects of the present invention.

The blind hole may be configured to receive a tubing connector in an unconnected state. The blind hole may be configured such that the blind hole is incapable of receiving a tubing connector that has two tubes extending therefrom in opposite directions. The blind hole may extend through a single face of the housing. The blind hole may be configured to receive a tubing connector by advancement along an axis substantially coaxial to a central axis of a lumen of the tubing connector.

The sterilization device may include timing logic operable to illuminate the ultraviolet light source for a predeterminable length of time. The predeterminable time may be calculated to kill or inactivate a predetermined percentage of microorganisms that may be disposed on the tube set connector. The sterilization device may include a reflective lining within the interior of the sterilization chamber. The ultraviolet light source may be operable to emit ultraviolet energy within the 200 nm to 280 nm wavelengths.

The sterilization device may include a tube set detection member (e.g., a sensor) operable to detect a portion of a tube set (e.g., the tube set connector) disposed within the housing. The illumination control logic may be operable to energize the ultraviolet light source to illuminate the sterilization chamber when the tube set detection member detects a portion of the tube set disposed within the housing. The illumination control logic may be operable to automatically illuminate the ultraviolet light source upon an insertion into the sterilization chamber.

The sterilization device may further include a locking mechanism operable to lock a tube set into place when a portion of the tube set (e.g., the tube set connector) is disposed within the housing and the ultraviolet light source is illuminated. The sterilization device may further include a timing module operable to illuminate the ultraviolet light source after the tube set connector has been disposed within the sterilization chamber for a predeterminable period of time.

The sterilization device may include a button or other appropriate input device that when activated by a user, would cause the illumination control logic to energize the ultraviolet light source. In this regard, a user may initiate the sterilization of a tube set connector disposed within the sterilization device.

Third, fourth, and fifth aspects of the present invention are each provided by a method of sterilizing a first connector fluidly interconnected to a fluid source. Each of these methods includes placing the first connector in an unconnected state into a chamber, and irradiating the first connector within the chamber with ultraviolet radiation. During the irradiating step, a tube fluidly interconnected to the first connector extends from the first connector to an exterior of the chamber.

In the case of the third aspect, the irradiating step occurs after the placing step, and the method further includes removing the first connector in an unconnected state from the chamber after the irradiating step. The unconnected state of the first connector is maintained during the entirety of time between the placing and removing steps.

In the case of the fourth aspect, the method further includes removing the first connector in an unconnected state from the chamber, then connecting the first connector to a second connector. The connecting step occurs outside of the chamber. The method further includes flowing fluid through the connected first and second connectors.

In the case of the fifth aspect, the method includes, prior to the placing step, disconnecting the first connector from a second connector. After the disconnecting step, the first connector is fluidly interconnected with the fluid source. The disconnecting step occurs outside of the chamber.

A number of feature refinements and additional features are applicable to the third, fourth, and fifth aspects of the present invention. These feature refinements and additional features may be used individually or in any combination. As such, each of the following features that will be discussed may be, but are not required to be, used with any other feature or combination of features of the third, fourth, and fifth aspects. The following discussion is applicable to the third, fourth, and fifth aspects, up to the start of the discussion of the term "fluidly interconnected."

Sterilizing the first connector may include storing the first connector within the chamber for a first period of time after the irradiating step and before removing the first connector from the chamber. The first connector may be irradiated within the chamber a second time after the storing step and prior to removing the first connector from the chamber. This repetition of the irradiating step may be automatically initiated if the first connector has not been removed from the chamber within a certain amount of time after an execution of the irradiating step.

After the placing step and prior to the irradiating step, a sensor may sense a presence of at least one of the first connector and the tube. The placing step may include advancing the first connector through an opening in the chamber along an axis substantially coaxial to a lumen through the first connector. The method may include securing the first connector within the chamber after the placing step and prior to and during the irradiating step. The irradiating step may be initiated by a user.

The method may include moving a member from a first position to a second position after the placing step and prior to the irradiating step. In the second position, the member may obstruct ultraviolet radiation attempting to exit the chamber. The irradiating step may be initiated automatically when the member reaches the second position.

In an embodiment, the method may include connecting the first connector to a syringe of a power injector, transferring fluid from the fluid source to the syringe through the first connector, detaching the first connector from the syringe of the power injector, and repeating the placing and irradiating steps. In such an arrangement, the connecting of the first connector to the syringe may occur after the irradiating step and may occur outside of the chamber. Furthermore, the transferring step may occur after connecting the first connector to the syringe.

In an embodiment, the method may include connecting the first connector to a patient-specific tube set connector, transferring fluid from the fluid source (e.g., a bulk fluid container fluidly interconnected to a power injector syringe) to a patient-specific tube set that includes the patient-specific tube set connector, detaching the first connector from the patient-specific tube set connector, and repeating the placing and irradiating steps. In such an arrangement, the connecting of the first connector to the patient-specific tube set connector may occur after the irradiating step and may occur outside of the chamber. Furthermore, the transferring step may occur after connecting the first connector to the patient-specific tube set connector. As such, the method may be implemented in the context of a multi-dose injection system, where one or more bulk fluid containers are fluidly interconnected with a multi-use tube set having the first connector, where this multi-use tube set is also fluidly interconnected with one or more power injector syringes, and where a number of single-use or patient-specific tube sets may be sequentially joined with the first connector (e.g., to sequentially inject multiple patients via operation of the power injector).

As used herein, the term "fluidly interconnected" refers to two or more components or entities being connected (directly or indirectly) in a manner such that fluid can flow (e.g., unidirectionally or bidirectionally) in a predetermined flow path therebetween. For example, "an injection device fluidly interconnected to a patient" describes a configuration where fluid can flow from the injection device through any interconnecting devices (e.g., tubing, connectors) and into the patient (e.g., Into the vasculature of the patient).

As used herein, the terms "detachably coupled" and the like describe a relationship between components where the components are coupled or interconnected yet retain the ability to be detached from each other where, after detaching, at least one of the components remains in a usable condition. For example, "a tube set connector and a bulk fluid container are detachably interconnected" describes a condition where the tube set connector is currently interconnected to the bulk fluid container in a manner that allows for the tube set connector to be detached from the bulk fluid container. Furthermore, after such detaching, at least one (e.g., both) of the bulk fluid container and the tube set connector retains the ability to be interconnected (e.g., detachably) with another component.

A number of feature refinements and additional features are separately applicable to each of above-noted first, second, third, fourth, and fifth aspects of the present invention. These feature refinements and additional features may be used individually or in any combination in relation to each of the above-noted first, second, third, fourth, and fifth aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical). Finally, a reference of a feature in conjunction with the phrase "in one embodiment" does not limit the use of the feature to a single embodiment.

Any "logic" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

Any multi-dose injection system may include any number of bulk containers of fluid. Such multi-dose injection systems may be used to deliver fluids from the bulk containers to multiple patients. The bulk containers may contain any appropriate type of fluid. The bulk containers may each contain a unique type of fluid or some or all of the bulk containers may contain the same type of fluid. The bulk containers may be fluidly interconnected to the multi-dose injection system via any appropriate number of valves. The bulk containers may be fluidly interconnected to any appropriate number of syringes.

DETAILED DESCRIPTION

Figure 1:
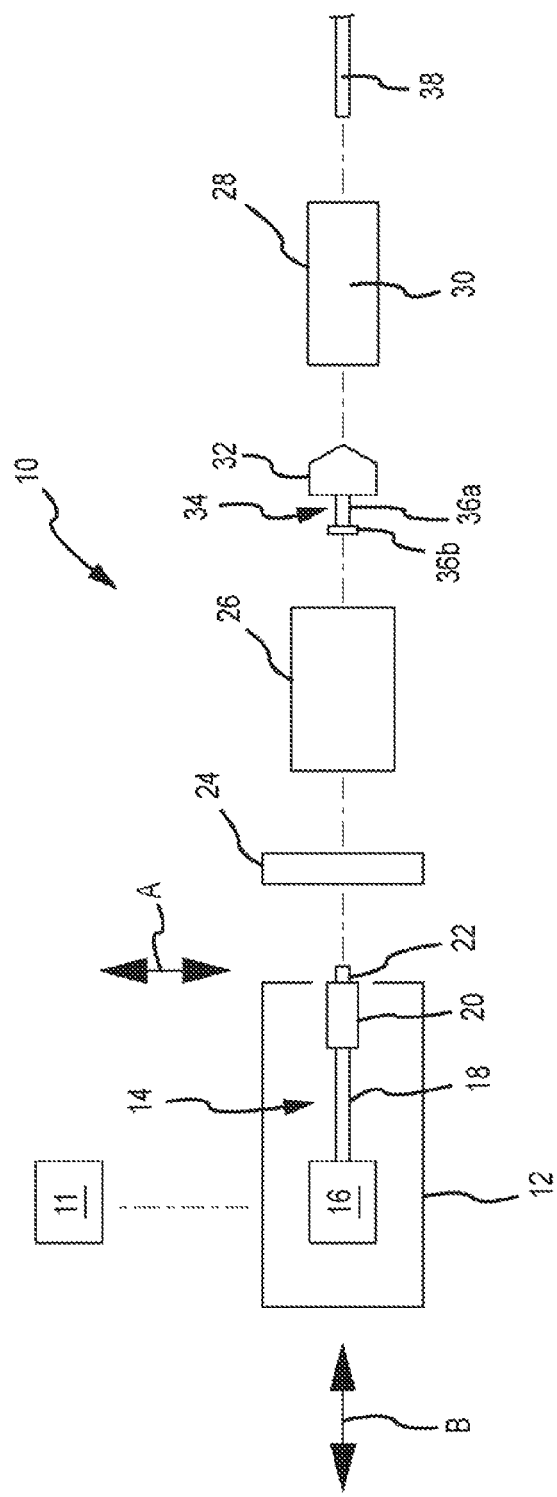
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
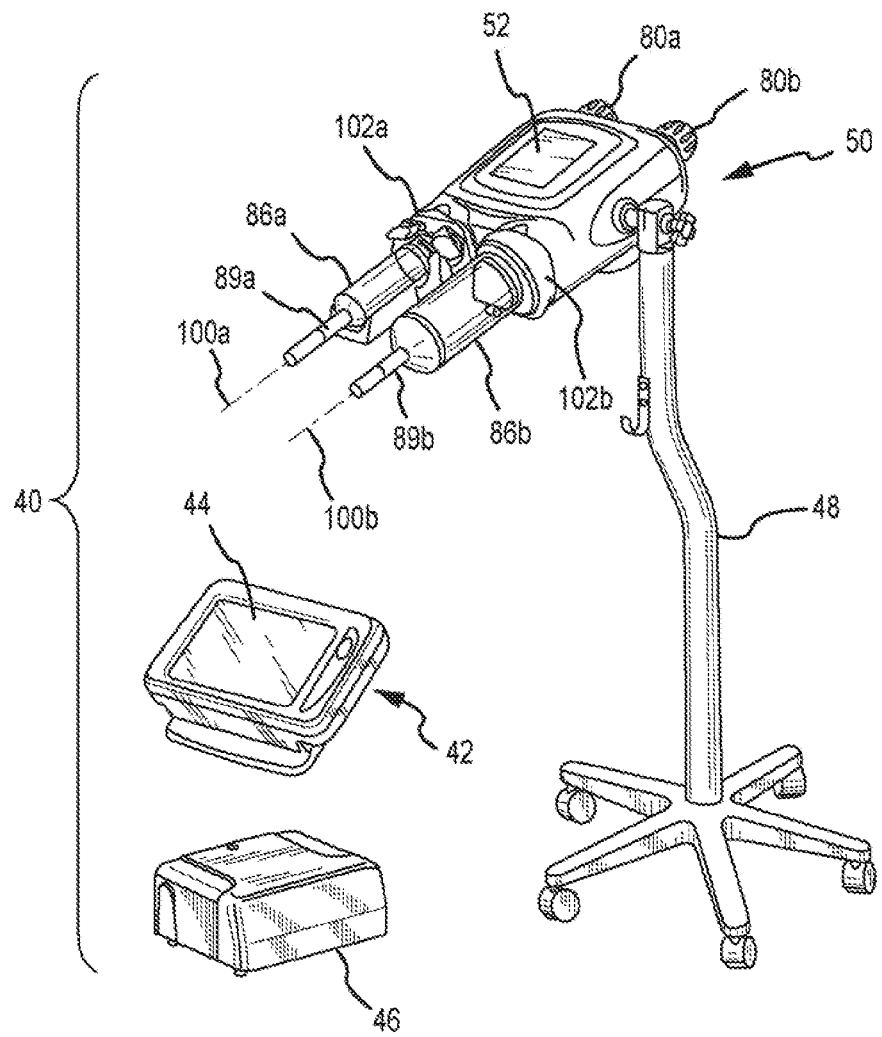
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86*a*, 86*b*, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative to the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply 46 for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
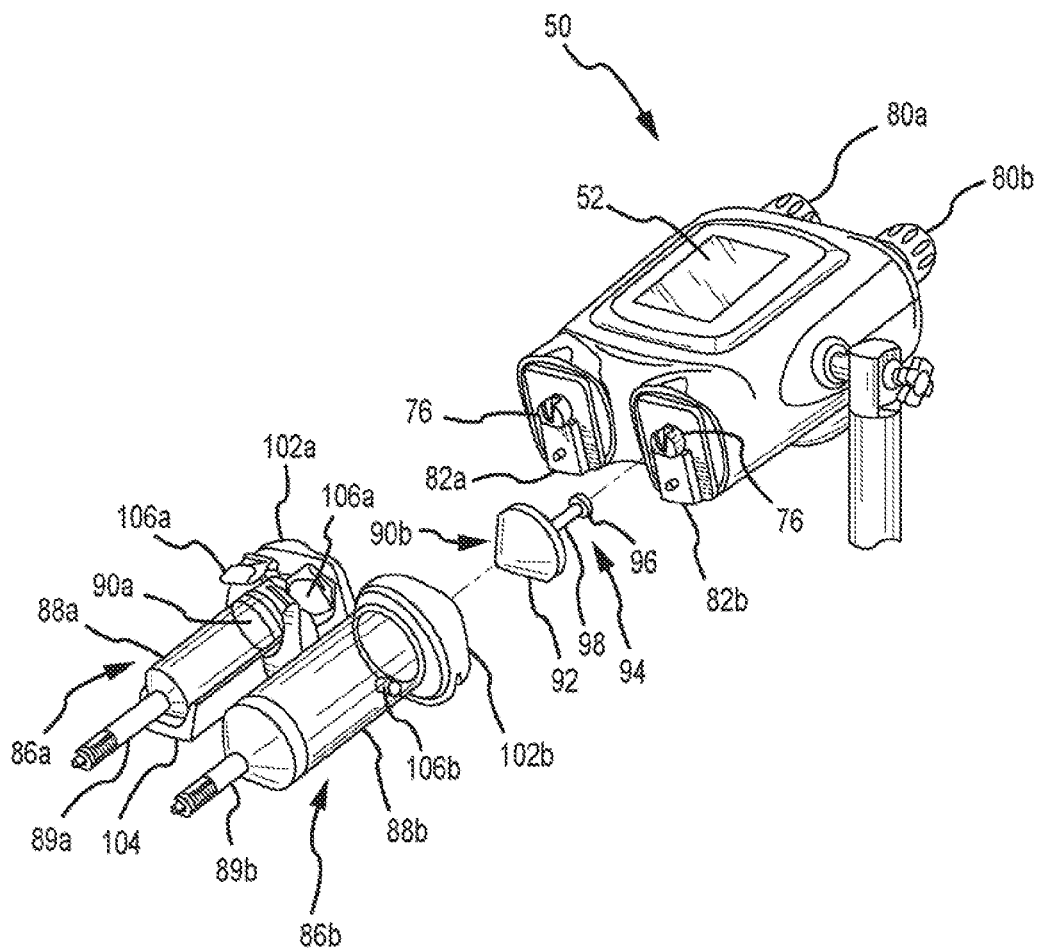
FIG. 2B is an enlarged, partially exploded, perspective view of a powerhead used by the power injector of FIG. 2A.

Various details regarding the integration of the syringes 86*a*, 86*b* with the powerhead 50 are presented in FIG. 2B. Each of the syringes 86*a*, 86*b* includes the same general components. The syringe 86*a* includes plunger or piston 90*a* that is movably disposed within a syringe barrel 88*a*. Movement of the plunger 90*a* along an axis 100*a* (FIG. 2A) via operation of the powerhead 50 will discharge fluid from within a syringe barrel 88*a* through a nozzle 89*a* of the syringe 86*a*. An appropriate conduit (not shown) will typically be fluidly interconnected with the nozzle 89*a* in any appropriate manner to direct fluid to a desired location (e.g., a patient). Similarly, the syringe 86*b* includes plunger or piston 90*b* that is movably disposed within a syringe barrel 88*b*. Movement of the plunger 90*b* along an axis 100*b* (FIG. 2A) via operation of the powerhead 50 will discharge fluid from within the syringe barrel 88*b* through a nozzle 89*b* of the syringe 86*b*. An appropriate conduit (not shown) will typically be fluidly interconnected with the nozzle 89*b* in any appropriate manner to direct fluid to a desired location (e.g., a patient).

The syringe 86*a* is interconnected with the powerhead 50 via an intermediate faceplate 102*a*. This faceplate 102*a* includes a cradle 104 that supports at least part of the syringe barrel 88*a*, and which may provide/accommodate any additional functionality or combination of functionalities. A mounting 82*a* is disposed on and is fixed relative to the powerhead 50 for interfacing with the faceplate 102*a*. A ram coupler 76 of a ram 74 (FIG. 2C), which are each part of a syringe plunger drive assembly or syringe plunger driver 56 (FIG. 2C) for the syringe 86*a*, is positioned in proximity to the faceplate 102*a* when mounted on the powerhead 50. Details regarding the syringe plunger drive assembly 56 will be discussed in more detail below in relation to FIG. 2C. Generally, the ram coupler 76 may be coupled with the syringe plunger 90*a* of the syringe 86*a*, and the ram coupler 76 and ram 74 (FIG. 2C) may then be moved relative to the powerhead 50 to move the syringe plunger 90*a* along the axis 100*a* (FIG. 2A). It may be such that the ram coupler 76 is engaged with, but not actually coupled to, the syringe plunger 90*a* when moving the syringe plunger 90*a* to discharge fluid through the nozzle 89*a* of the syringe 86*a*.

The faceplate 102*a* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*a* on and remove the faceplate 102*a* from its mounting 82*a* on the powerhead 50. The faceplate 102*a* may be used to couple the syringe plunger 90*a* with its corresponding ram coupler 76 on the powerhead 50. In this regard, the faceplate 102*a* includes a pair of handles 106*a*. Generally and with the syringe 86*a* being initially positioned within the faceplate 102*a*, the handles 106*a* may be moved to in turn move/translate the syringe 86*a* at least generally within a plane that is orthogonal to the axes 100*a*, 100*b* (associated with movement of the syringe plungers 90*a*, 90*b*, respectively, and illustrated in FIG. 2A). Moving the handles 106*a* to one position moves/translates the syringe 86*a* (relative to the faceplate 102*a*) in an at least generally downward direction to couple its syringe plunger 90*a* with its corresponding ram coupler 76. Moving the handles 106*a* to another position moves/translates the syringe 86*a* (relative to the faceplate 102*a*) in an at least generally upward direction to uncouple its syringe plunger 90*a* from its corresponding ram coupler 76.

The syringe 86*b* is interconnected with the powerhead 50 via an intermediate faceplate 102*b*. A mounting 82*b* is disposed on and is fixed relative to the powerhead 50 for interfacing with the faceplate 102*b*. A ram coupler 76 of a ram 74 (FIG. 2O), which are each part of a syringe plunger drive assembly 56 for the syringe 86*b*, is positioned in proximity to the faceplate 102*b* when mounted to the powerhead 50. Details regarding the syringe plunger drive assembly 56 again will be discussed in more detail below in relation to FIG. 2C. Generally, the ram coupler 76 may be coupled with the syringe plunger 90*b* of the syringe 86*b*, and the ram coupler 76 and ram 74 (FIG. 2O) may be moved relative to the powerhead 50 to move the syringe plunger 90*b* along the axis 100*b* (FIG. 2A). It may be such that the ram coupler 76 is engaged with, but not actually coupled to, the syringe plunger 90*b* when moving the syringe plunger 90*b* to discharge fluid through the nozzle 89*b* of the syringe 86*b*.

The faceplate 102*b* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
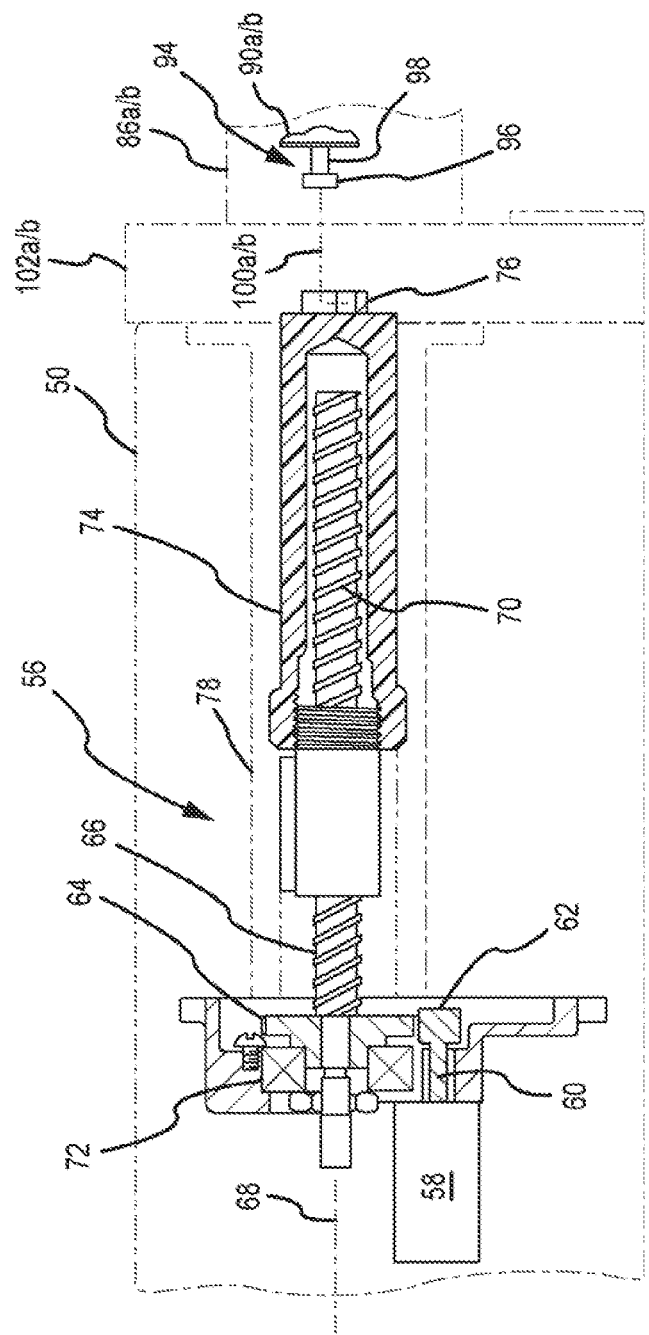
FIG. 2C is a schematic of one embodiment of a syringe plunger drive assembly used by the power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86*a/b*, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient), Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3A:
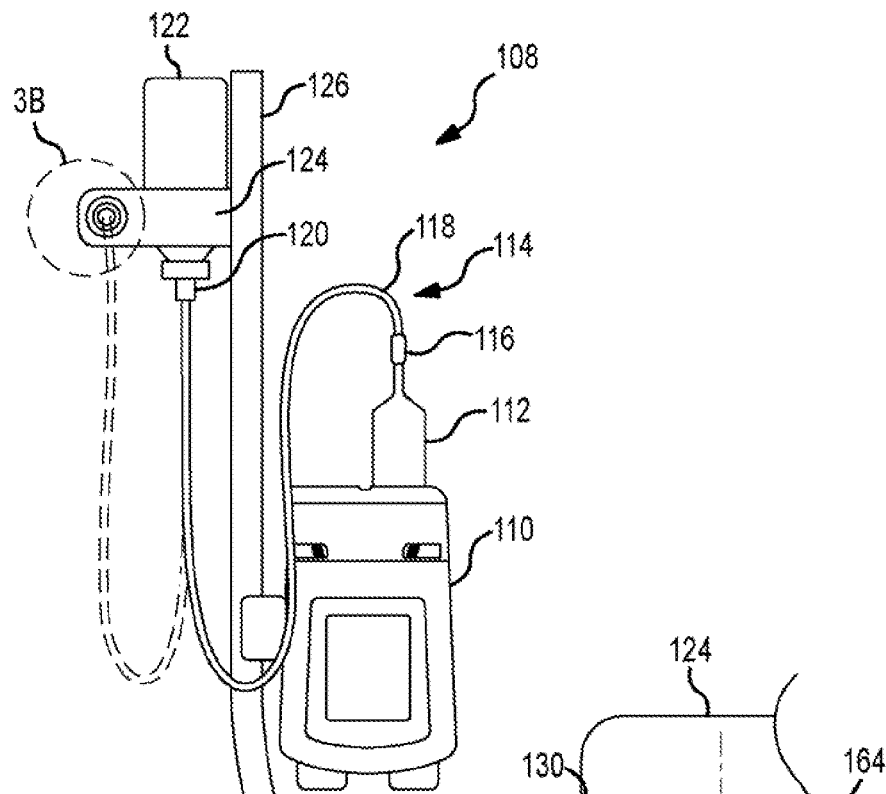
FIGS. 3A and 3B are illustrations of an injection system that include a sterilization port.
Figure 3B:
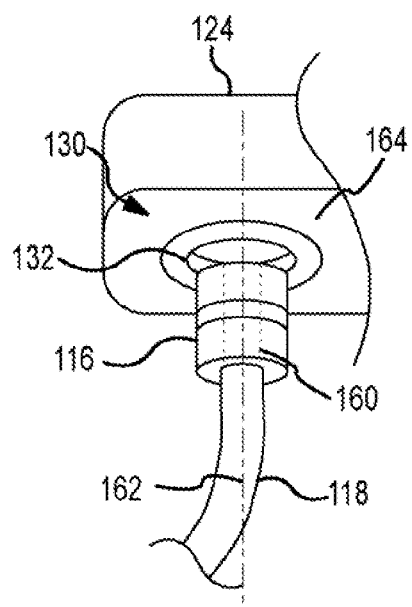

FIGS. 3A and 3B illustrate an injection system 108 that includes a sterilization port 130. In FIG. 3A, the injection system 108 includes a powerhead 110 operable to control (e.g., expand and/or retract) a plunger disposed within a syringe 112. The syringe 112 may be fillable by interconnecting the syringe 112 to a fluid source 122. Such a connection may be achieved with a tube set 114. The tube set 114 may include a tube set connector 116 operable to interconnect to a fluid port of the syringe 112. In turn, the tube set connector 116 may be fluidly interconnected to tubing 118, which may in turn be fluidly interconnected to a fluid source connector 120. The fluid source connector 120 may be fluidly interconnected to the fluid source 122. In this regard, the fluid source 122 may be fluidly interconnected to the syringe 112. The fluid source 122 may be supported and held in position by a fluid source support member 124. The powerhead 110 and the fluid source support member 124 may be interconnected to and supported by a support 126. Alternatively, the fluid source support member 124 and the powerhead 110 may be independently supported in any appropriate manner. The fluid source member 122 could also be hand-held during loading of the syringe 112.

The fluid source 122 of the injection system 108 may be used to fill a plurality of different syringes 112 in succession. For each of syringe 112 to be filled, the tube set 114 may be interconnected to the syringe 112 to be filled via the tube set connector 116. Between interconnections to successive syringes 112, the tube set connector 116 may be exposed to potential contamination. Accordingly, it may be beneficial to sterilize the tube set connector 116 between interconnections to successive syringes 112.

As illustrated in FIG. 3B, the fluid source support member 124 may include the sterilization port 130. Alternatively, the sterilization port 130 may be disposed in any appropriate location and/or be attached to any appropriate component of the injection system 108. The sterilization port 130 may be in the form of a stand-alone device. The sterilization port 130 may include a sterilization port opening 132 through which the tube set connector 116 may be inserted while the tube set connector 116 is in an unconnected state (e.g., the tube set connector 116 has the tubing 118 attached thereto, but no mating connector is attached to the tube set connector 116—as illustrated in FIG. 3B). The sterilization port 130 may be sized to accept at least a portion of the tube set connector 116 such that appropriate portions of the tube set connector 116 may be disposed within the sterilization port 130 and sterilized. The sterilization port 130 may be in the form of a blind hole. As used herein, "blind hole" refers to a hole that does not pass completely through an object. In this regard, a "blind hole" has a single opening between the environment external to an object (e.g., such as the fluid source support member 124) and the internal volume of the hole (e.g., a sterilization chamber (FIG. 5)). The sterilization port 130 may be in the form of a blind hole where the sterilization port opening 132 is disposed entirely within a single face 164 (FIG. 3B) of the fluid source support member 124.

As illustrated in FIG. 3B, the tube set connector 116 may be inserted through the sterilization port opening 132 by advancing the tube set connector 116 in a direction substantially coaxial to a central axis 162 of the tube set connector 116. The sterilization port opening 132 may be sized such that the tube set connector 116, while attached to tubing 118, may only pass through the sterilization port opening 132 by advancing the tube set connector 116 in a direction substantially coaxial to the central axis 162. In this regard, the sterilization port opening 132 may be sized and shaped to correspond to a cross section of the tube set connector 116 (e.g., the sterilization port opening 132 may be round and slight larger than the round cross section of the tube set connector 116). Furthermore, the tube set connector 116 may be incapable of passing through the sterilization port opening 132 when in a connected state (e.g., when connected to a mating connector that is connected to tubing). The central axis 162 may be substantially coaxial to a lumen 160 passing through the center of the tube set connector 116.

The sterilization port 130 may include a tube set holder 196 (FIG. 5), which may be in the form of a mechanical device to hold the free end of the tube set 114 that includes the tube set connector 116. For example, the sterilization port 130 may be sized to accept the entirety of the tube set connector 116, and may include a mechanical feature such as a keyed slot on which the tube set connector 116 may be hooked such that the position of the tube set connector 116 within the sterilization port 130 may be maintained.

Figure 3C:
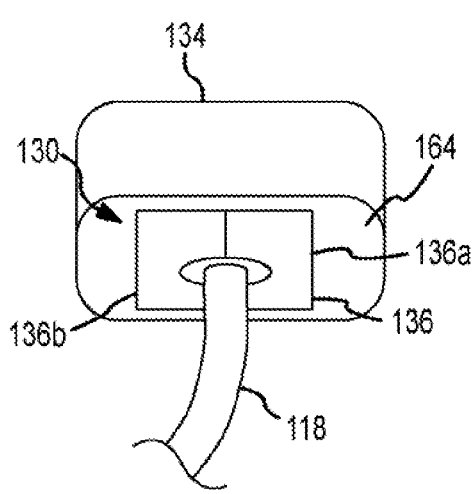
FIG. 3C is an illustration of a sterilization device.

FIG. 3C illustrates a sterilization device 134 that includes the sterilization port 130. The sterilization device 134 may be used in conjunction with the injection systems described herein. The sterilization device 134 may include a movable member or door 136 operable to close over a portion of the sterilization port opening 132 (not visible behind the door 136 in FIG. 3C) and around the tubing 118 to limit the amount of ultraviolet light escaping from within the sterilization port 130. The door 136 may be spring-loaded, actively moved (e.g., via a drive mechanism), or controlled in any other appropriate fashion. The door 136 may close around the tubing 118 by sliding along the face 164 of the sterilization device 134, by pivoting on a hinge or hinges attached to the face 164, or by any other appropriate means. The door 136 may be constructed of a pliable material that may deform or deflect when the tube set connector 116 is inserted into the sterilization port 130 and return to a shape (e.g., as shown in FIG. 3C) such that the door 136 is operable to obstruct light attempting to escape from the sterilization port 130 when the tube set connector 116 is fully inserted into the sterilization port 130. The door 136 may be a unitary member or it may include multiple components such as panels 136a and 136b illustrated in FIG. 3C. The sterilization port 130 of FIGS. 3A and 3B may also include a door 136 (not shown in FIGS. 3A and 3B).

The sterilization port 130 may be operable to receive any appropriate connector or portion of tube set 114. The sterilization port 130 may include a locking mechanism 192 (FIG. 5) operable to lock the tube set 114 into place (e.g., to prevent removal of the tube set 114 from the sterilization port 130) when a portion of the tube set 114 (e.g., tube set connector 116) is disposed within the sterilization port 130 and an ultraviolet light source 158 (FIGS. 4 and 5) is illuminated or activated. The above-described door 136 may also serve as the locking mechanism 192.

The ultraviolet light source 158 (FIGS. 4 and 5) may be disposed within the sterilization port 130. The sterilization port 130 may be used kill or inactivate microorganisms (e.g., viruses, bacteria, mold) on members inserted therein through exposure to ultraviolet light emitted from the ultraviolet light source 158. The ultraviolet light source 158 may emit a germicidal ultraviolet light (200 nm to 280 nm) that can be turned on for a specific amount of time. The interior of the sterilization port 130 may be lined with a highly reflective material in the form of a reflective lining 178 (FIG. 5) to reflect ultraviolet light emitted from the ultraviolet light source 158 onto members inserted into the sterilization port 130.

In addition to or in place of the above-described door 136, the sterilization port 130 may include any appropriate member to limit the amount of light that may escape from the sterilization port 130 through the sterilization port opening 132. For example, the sterilization port opening 132 may be lined with a plurality of bendable members (e.g., similar to bristles of a paintbrush) operable to conform to the portion of the tube set 114 (e.g., tube set connector 116) disposed in the sterilization port opening 132 and also limit the amount of ultraviolet light escaping from the sterilization port 130.

The sterilization port 130 may also include one or more sensors operable to control certain functions of the sterilization port 130. For example, the sterilization port 130 may include a tube set detection member 194 (FIG. 5) (e.g., a sensor) operable to detect whether or not a member is disposed within the sterilization port 130. Output from the tube set detection member 194 may be used by illumination control logic 182 (FIG. 5) to determine whether or not to energize the ultraviolet light source 158. The illumination control logic 182 may also prevent the ultraviolet light source 158 from being energized (e.g., from emitting ultraviolet light) when no object has been inserted into the sterilization port 130.

The sterilization port 130 may include timing logic 180 (FIG. 5) operable to illuminate the ultraviolet light source 158 for a predeterminable length of time. The sterilization port 130 may be operable to automatically illuminate the ultraviolet light source 158 upon an insertion into the sterilization port 130 for the predetermined amount of time.

Accordingly, in an exemplary embodiment, between interconnections of the tube set connector 116 to successive syringes 112, the tube set connector 116 may be inserted into the sterilization port 130 for sterilization. The sterilization port 130 may detect an insertion of the tube set connector 116. The movable member 136 may be closed over a portion the sterilization port opening 132. Upon detection of the insertion and/or closing of the movable member 136, the sterilization port 130 may automatically illuminate the ultraviolet light source 158 for a predetermined period of time to sterilize the tube set connector 116. Upon completion of the predetermined period of time, the ultraviolet light source 158 may be turned off. In this manner, the tube set connector 116 may be sterilized between attachments to successive syringes 112.

The sterilization port 130 may be used to sterilize members under a variety of different usage scenarios. In a first example, referring to FIG. 3A, the injection system 108 may be used to serially deliver fluids to a plurality of patients through a series of patient-specific tube sets (not shown in FIG. 3A). After loading the syringe 112 with fluid from the fluid source 122, the tube set connector 116 may be disconnected from the syringe 112 and inserted into the sterilization port 130 for sterilization. Then a patient-specific tube set (not shown) may be interconnected to the syringe 112 and fluid from the syringe 112 may be delivered to a patient. After delivery of fluid to the patient, the patient-specific tube set may be disconnected from the patient and syringe 112 and discarded. A new syringe 112 may then be installed onto the powerhead 110, and the sterilized tube set connector 116 may be removed from the sterilization port 130 and attached to the new syringe 112. It may be desirable to sterilize the tube set connector 116 via the sterilization port 130 just prior to interfacing the tube set connector 116 with a new syringe 112. In any case, the new syringe 112 may be loaded with fluid from the fluid source 122, and the process may be repeated.

Figure 4:
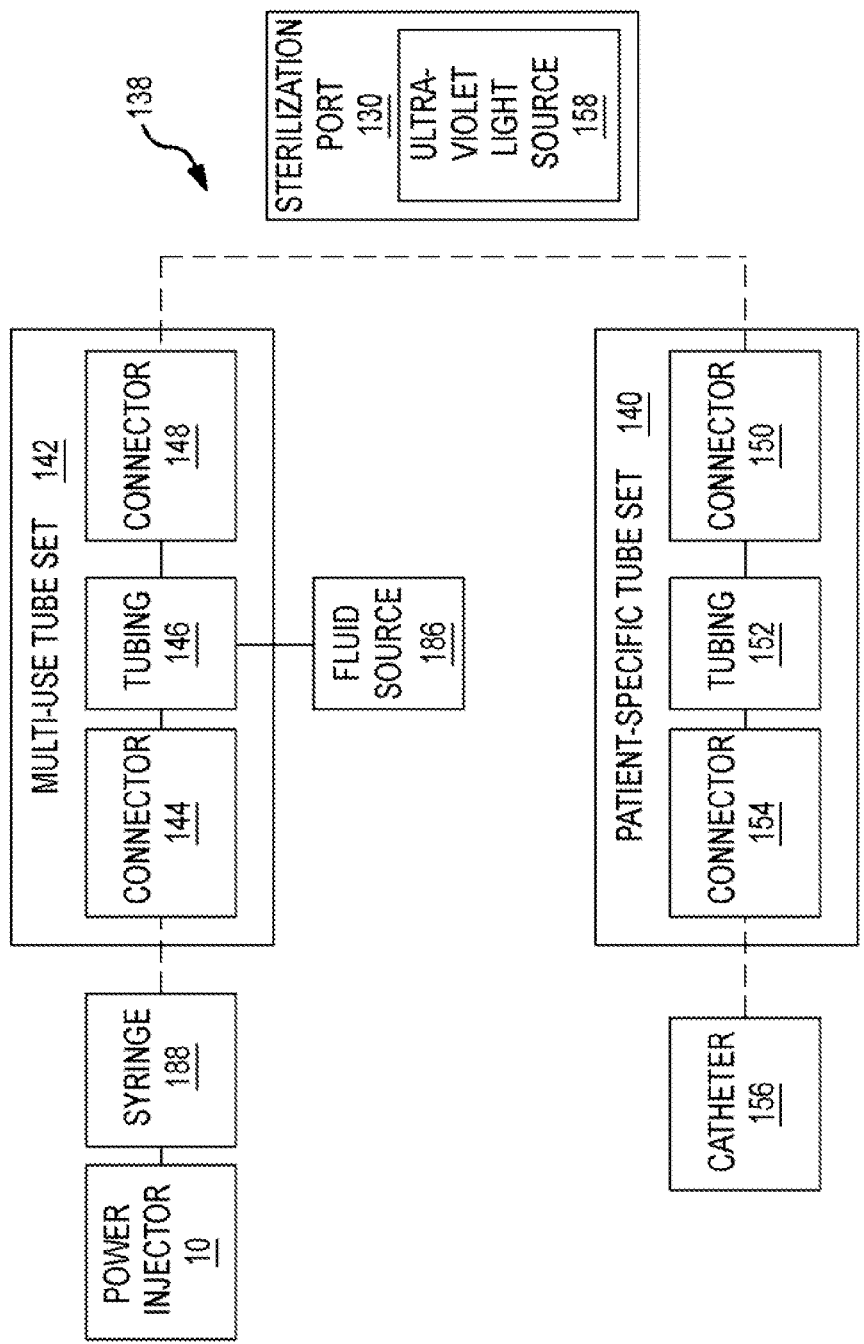
FIG. 4 is a block diagram of an embodiment of an injection system that includes a sterilization port.

FIG. 4 illustrates a second example of the integration of the sterilization port 130 with an injection system 138. FIG. 4 is a block diagram of an embodiment of the injection system 138 that includes the sterilization port 130. The injection system 138 of FIG. 4 is a multi-use injection system operable to inject fluids successively into a plurality of patients while maintaining fluid interconnection to a bulk fluid source 186. This is, in part, achieved by the use of a patient-specific tube set 140 interconnected to each individual patient, where a multi-use tube set 142 is used multiple times to interconnect the power injector 10 and bulk fluid source 186 to multiple patient-specific tube sets 140.

In the injection system 138, the syringe 188 is interconnected to the power injector 10. The syringe 188 may be interconnected to the multi-use tube set 142 by a connector 144 of the multi-use tube set 142. The connector 144 may in turn be fluidly interconnected with tubing 146 of the multi-use tube set 142, which may be fluidly interconnected to the bulk fluid source 186 and another connector 148. The multi-use tube set 142 may include other connectors and/or tubing sections and/or valves to control the flow of fluid therethrough. For example, the multi-use tube set 142 may include a Y connector, with additional tubing, to interconnect the power injector 10 to the bulk fluid source 186.

The patient-specific tube set 140 may include a connector 150 for connection to the connector 148 of the multi-use tube set 142. Furthermore, the patient-specific tube set 140 may include tubing 152 and another connector 154 for connection to a catheter 156 (e.g., inserted into the patient). Any appropriate vasculature access device may be utilized.

The injection system 138 may further include the sterilization port 130. The sterilization port 130 may be disposed in any appropriate location. For example, the sterilization port 130 may be disposed in a bulk container holder module, within the power injector 10, or the sterilization port 130 may be a stand-alone component (e.g., a sterilization device).

As noted, the connector 148 of the multi-use tube set 142 may be used to connect to successive patient-specific tube sets 140 as fluid is delivered to successive patients through the multi-use tube set 142. Accordingly, the connector 148 may be sterilized using the sterilization port 130 in the manner described above (with reference to tube set connector 116) between successive connections to successive patient-specific tube sets 140. In this regard, the connector 148 may be sterilized between fluid deliveries to successive patients.

Additionally, any appropriate connector of the injection system 138 may be sterilized using the sterilization port 130 at any appropriate time. For example, the connector 150 of the patient-specific tube set 140 may be sterilized using the sterilization port 130 prior to interconnection to the connector 148 of the multi-use tube set 142. For further example, the connector 144 of the multi-use tube set 142 used to interconnect to the syringe 188 may be sterilized using the sterilization port 130 prior to such an interconnection.

The sterilization port 130 may be operable to re-sterilize a particular member (e.g., connector 148) if the particular member has been disposed within the sterilization port 130 for a predetermined amount of time. For example, a user may place the member into the sterilization port 130 and the member may be sterilized by the ultraviolet light source 158. After sterilization, the ultraviolet light source 158 may be deactivated. If the member is allowed to remain within the sterilization port 130 for a predetermined amount of time (e.g., an hour), the sterilization port 130 may automatically re-sterilize the member. In this regard, a member disposed in the sterilization port 130 may be periodically re-sterilized and therefore remain in a ready-to-use condition. Accordingly, a timing module 198 (FIG. 5) may be operable to re-activate the ultraviolet light source 158 after a member has been disposed within the sterilization port 130 for a predetermined amount of time.

The connectors described herein with reference to FIGS. 3A, 3B, 4 and 5 may be of any appropriate type or types. For example, one or more of the connectors may be Luer connectors. In this regard, this sterilization port 130 may be configured to receive and sterilize Luer connectors.

Figure 5:
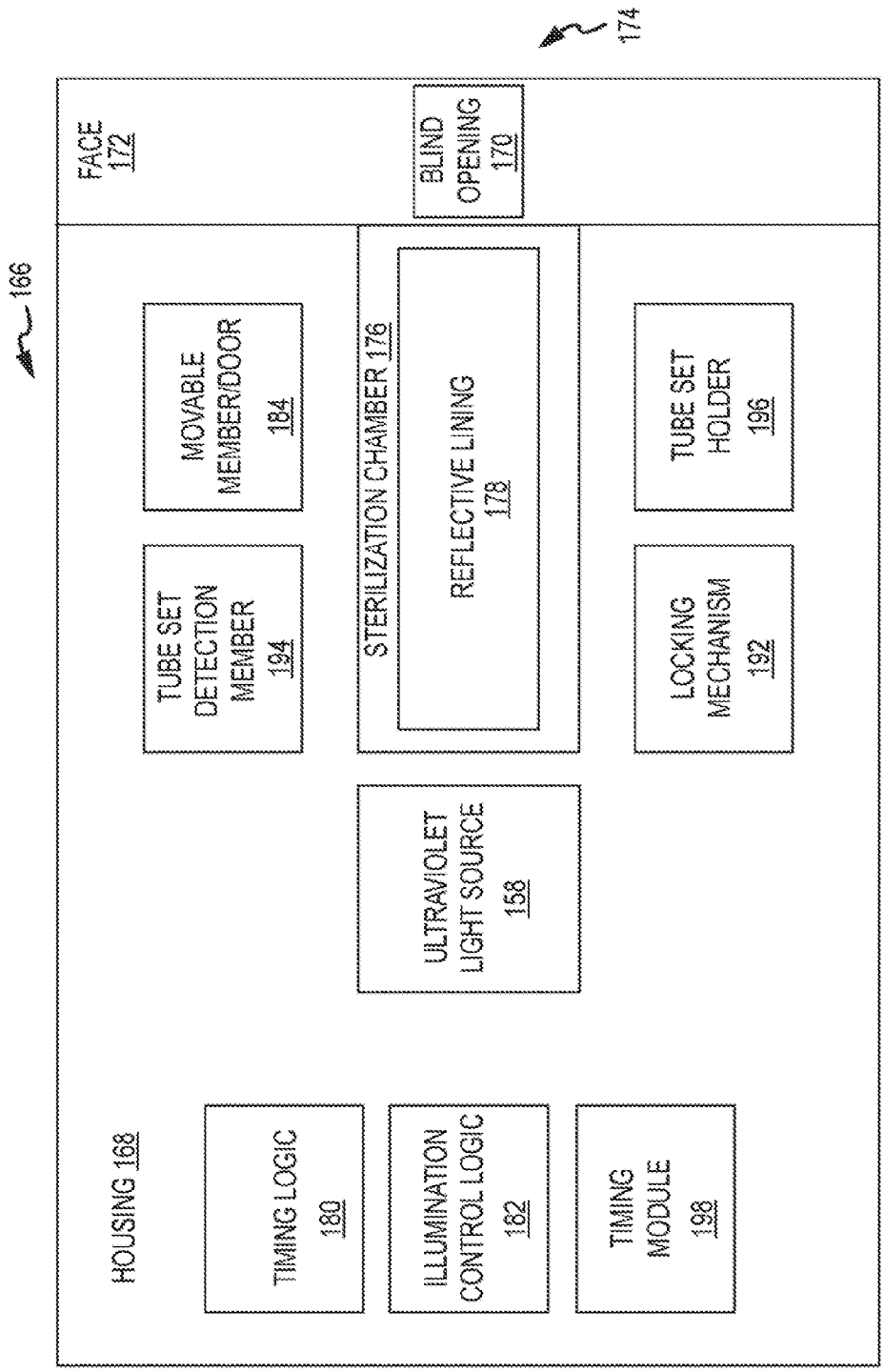
FIG. 5 is a block diagram of an embodiment of a sterilization device.

FIG. 5 is a block diagram of a sterilization device 166 that may be used to sterilize the tube set connectors described herein. The sterilization device 166 may include a housing 168. A sterilization chamber 176 may be disposed within the housing 168. The sterilization chamber 176 may include a reflective lining 178 to aid in distributing ultraviolet light from the ultraviolet light source 158. The sterilization device 166 may include a blind hole 174 that includes a blind opening 170 through a single face 172 of the housing 168 and that extends into the interior of the sterilization chamber 176. In this regard, the blind hole 174 may be the only hole extending into the housing 168 and into the sterilization chamber 176 that a connector would be capable of passing through.

As noted earlier, the sterilization device 166 may include a movable member or door 184, a locking mechanism 192, and/or a tube set holder 196. In a particular embodiment, any two or three of these items may be combined. For example, the movable member 184 and locking mechanism 192 may be a single mechanism capable of performing both a door function (e.g., limiting ultraviolet light from escaping from the sterilization chamber 176) and a locking function (e.g., aiding in preventing removal of a connector from within the sterilization chamber 176). In another example, all three items may be combined in a single device or assembly.

The sterilization device 166 may include the tube set detection member 194 (e.g., sensor). The sterilization device 166 may include the aforementioned illumination control logic 182, timing logic 180, and timing module 198. Alternatively, one or more of the illumination control logic 182, timing logic 180, and timing module 198 may be disposed external to the sterilization device 166 and control the corresponding function of the sterilization device 166 remotely.

Figure 6:
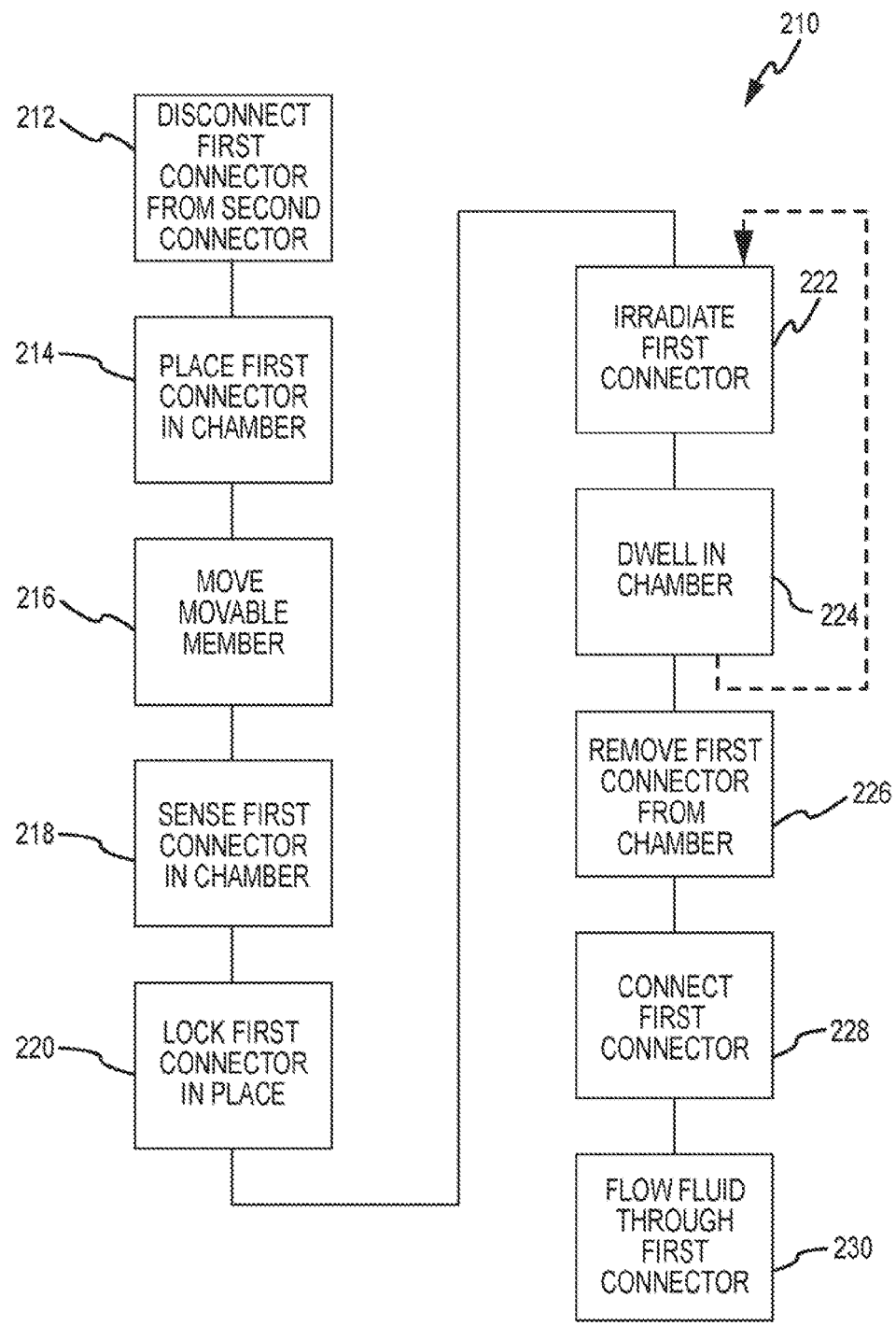
FIG. 6 is a flowchart of a method of sterilizing a connector.

FIG. 6 is a flowchart of a method of sterilizing a first connector that is fluidly interconnected to a fluid source of any appropriate type (e.g., a bulk fluid source; a syringe). The first step 212 in the illustrated method is to disconnect a first connector from a second connector. The first connector is fluidly interconnected to a fluid source and may be reused a plurality of times. In the case where a bulk fluid supply is used to load fluid into multiple syringes (e.g., illustrated in FIG. 3A), the second connector may be at a nozzle of a syringe. In the case where the first connector is part of a multi-use tube set, the second connector may be a connector of a patient-specific tube set (e.g., illustrated in FIG. 4). The disconnecting in step 212 may be performed outside of the sterilization device (e.g., the sterilization port 130, sterilization device 166).

The next step 214 may be to place the first connector inside a sterilization chamber of the sterilization device. This step 214 may be completed with the first connector in an unconnected state. The first connector may be advanced into the sterilization chamber along an axis substantially coaxial to a lumen through the first connector. Such an axis may be perpendicular to a plane of an opening into the sterilization chamber.

Where the sterilization device is equipped with a movable member or door, the next step 216 may be to move the movable member such that it closes around the first connector and/or a tube attached to the first connector to reduce the amount of ultraviolet light that may escape the sterilization chamber. Movement of the movable member may be performed manually or automatically. Where the sterilization device is equipped with a sensor, the next step 218 may be to sense the first connector and/or a tube attached to the first connector to determine that the first connector has been inserted into the sterilization chamber. Where the sterilization device is equipped with a locking mechanism, the next step 220 may be to lock the first connector into place within the sterilization chamber. Such locking may aid in hindering removal of the first connector from the sterilization chamber at undesirable times (e.g., when the ultraviolet light source is illuminated). Steps 214, 216 and 218 may be performed in any order or may be performed simultaneously.

Once the first connector has been properly placed into the sterilization chamber, the next step 222 may be to irradiate the first connector with ultraviolet radiation by illuminating an ultraviolet light source interconnected to the sterilization chamber. During irradiation, the tube fluidly interconnected with the first connector may extend from the first connector to an exterior of the sterilization device. Such a tube may be the only tube extending from the interior of the sterilization device to the exterior of the sterilization device. The step 222 of irradiating may be initiated automatically upon predetermined events. For example, the ultraviolet light source may be illuminated once the sensor senses that the first connector is properly inserted into the sterilization chamber and/or once the movable member is moved to a closed position. The step 222 of irradiating may be initiated by a user of the sterilization device. For example, after properly placing the first connector into the sterilization chamber, the user may press a button to start an irradiation sequence. The step 222 of irradiating may include illuminating the ultraviolet light source for a predetermined period of time as discussed above.

After the step 222 of irradiating is complete, the user may remove the first connector or, as shown in step 224, the first connector may be allowed to dwell within the sterilization chamber. Dwelling within the sterilization chamber may be desirable where the first connector is not to be used immediately or after a short delay. After dwelling within the sterilization chamber for a predetermined amount of time (e.g., 15 minutes, 1 hour), the sterilization device may automatically return to step 222 and irradiate the first connector. By periodically irradiating the first connector, the sterility of the first connector, and also its readiness for use, may be maintained.

When the first connector is to be used again, the next step 226 may be to remove the first connector from the sterilization chamber. During the removing step 226, the first connector may be in an unconnected state. Moreover, during the entirety of the time from step 214 (inclusive) through completion of step 226, the first is connector may be in an unconnected state. That is, the first connector may be placed into the sterilization chamber in an unconnected state and may remain in the unconnected state until after removal from the sterilization chamber.

After removal, the next step 228 may be to connect the first connector to another connector. In the case where a bulk fluid supply is used to load fluid into multiple syringes (e.g., illustrated in FIG. 3A), the other connector may be at a nozzle of a syringe. In the case where the first connector is part of a multi-use tube set, the other connector may be a connector of a patient-specific tube set (e.g., illustrated in FIG. 4). The connecting in step 228 may be performed outside of the sterilization device.

After connection in step 228, the next step 230 may be to flow fluid through the connected first connector. In the case where a bulk fluid supply is used to load fluid into multiple syringes (e.g., illustrated in FIG. 3A), the flow may be into the syringe to load the syringe with fluid (e.g., in preparation for fluid delivery to a patient). In the case where the first connector is part of a multi-use tube set, the flow may be into the patient-specific tube set (e.g., illustrated in FIG. 4) and subsequently through a catheter and into a patient. After the step 230 of flowing fluid is complete, the method may be repeated by returning to step 212 and disconnecting the other connector from the first connector.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An injection system comprising:
a fluid source;
a power injector;
a syringe interconnected with said power injector;
a tube set comprising a tube set connector, wherein said tube set is fluidly interconnected with said fluid source, and wherein said tube set connector is interconnectable with said syringe; and
a sterilization port, said sterilization port being configured to receive said tube set connector when disconnected from said syringe, said sterilization port comprising an ultraviolet light source, wherein said sterilization port comprises a blind opening to an interior of said sterilization port, and wherein said blind opening is the only opening to access said interior of said sterilization port.

2. The injection system of claim 1, further comprising illumination control logic that controls said ultraviolet light source.

3. The injection system of claim 2, further comprising a door movable between open and closed positions, said door being disposed about a perimeter of a tube of said tube set when said tube set connector is disposed within said sterilization port and when said door is in said closed position.

4. The injection system of claim 3, wherein said illumination control logic prevents said ultraviolet light source from illuminating said interior of said sterilization port when said door is in said open position, and wherein said illumination control logic energizes said ultraviolet light source to illuminate said interior of said sterilization port when said door is in said closed position.

5. The injection system of claim 2, further comprising a tube set detection member that detects when a portion of said tube set is disposed within said sterilization port.

6. The injection system of claim 5, wherein said illumination control logic energizes said ultraviolet light source to illuminate said interior when said tube set detection member detects that said portion of said tube set is disposed within said sterilization port.

7. The injection system of claim 2, wherein said illumination control logic automatically illuminates said ultraviolet light source upon insertion of said tube set connector into said sterilization port.

8. The injection system of claim 1, further comprising timing logic that illuminates said ultraviolet light source for a predetermined length of time.

9. The injection system of claim 1, further comprising a tube set holder disposed at said blind opening of said sterilization port, wherein said tube set holder secures said tube set such that a position of said tube set connector within said sterilization port is maintained.

10. The injection system of claim 1, further comprising a reflective lining within an interior of said sterilization port.

11. The injection system of claim 1, wherein said ultraviolet light source emits ultraviolet energy within the 200 nm to 280 nm wavelengths.

12. The injection system of claim 1, further comprising a locking mechanism that locks said tube set into place when a portion of said tube set is disposed within said sterilization port.

13. The injection system of claim 1, further comprising a timing modules that illuminates said ultraviolet light source after said tube set connector has been disposed within said sterilization port for a predetermined period of time.

14. The injection system of claim 1, wherein said blind opening corresponds to a cross section of said tube set connector.

15. The injection system of claim 1, further comprising a housing, wherein said sterilization port is disposed within said housing, and wherein said blind opening extends through a single face of said housing.

16. The injection system of claim 1, wherein said tube set connector comprises a lumen passing therethrough, wherein said lumen is disposed along an axis of said tube set connector, and wherein said tube set connector is only able to enter said interior of said sterilization port by advancing said tube set connector along said axis.

17. The injection system of claim 1, further comprising a fluid support member that supports said fluid source and that comprises said sterilization port.

18. An injection system comprising:
a fluid source;
a power injector;
a syringe interconnected with said power injector;
a multi-use tube set fluidly interconnected with each of said fluid source and said syringe, wherein said multi-use tube set comprises a first connector;
a patient-specific tube set comprising a second connector connected to said first connector of said multi-use tube set for execution of an injection procedure, wherein a tube set comprises each of said multi-use tube set and said patient-specific tube set, and wherein each of said first and second connectors is a separate tube set connector; and
a sterilization port, said sterilization port being configured to separately receive each of said first and second connectors at different times when said first and second connectors are disconnected from each other and with only one of said first and second connectors being positionable within said sterilization port at a time, wherein said sterilization port comprises an ultraviolet light source, wherein said sterilization port comprises a blind opening to an interior of said sterilization port, and wherein said blind opening is the only opening to access said interior of said sterilization port.

19. The injection system of claim 18, further comprising illumination control logic that controls said ultraviolet light source.

20. The injection system of claim 19, further comprising a door movable between open and closed positions, said door being disposed about a perimeter of a tube of said tube set when a single said tube set connector of said tube set is disposed within said sterilization port and when said door is in said closed position.

21. The injection system of claim 20, wherein said illumination control logic prevents said ultraviolet light source from illuminating said interior of said sterilization port when said door is in said open position, and wherein said illumination control logic energizes said ultraviolet light source to illuminate said interior of said sterilization port when said door is in said closed position.

22. The injection system of claim 19, further comprising a tube set detection member that detects when a portion of said tube set is disposed within said sterilization port.

23. The injection system of claim 22, wherein said illumination control logic energizes said ultraviolet light source to illuminate said interior when said tube set detection member detects that said portion of said tube set is disposed within said sterilization port.

24. The injection system of claim 19, wherein said illumination control logic automatically illuminates said ultraviolet light source upon insertion of a single said tube set connector into said sterilization port.

25. The injection system of claim 18, further comprising a timing module that illuminates said ultraviolet light source after a single said tube set connector has been disposed within said sterilization port for a predetermined period of time.

* * * * *